United States Patent [19]

Neefe

[11] 4,268,132

[45] May 19, 1981

[54] OXYGEN GENERATING CONTACT LENS

[76] Inventor: Charles W. Neefe, P.O. Box 429, Big Spring, Tex. 79720

[21] Appl. No.: 78,171

[22] Filed: Sep. 24, 1979

[51] Int. Cl.³ .............................................. G02C 7/04
[52] U.S. Cl. .............................................. 351/160 H
[58] Field of Search .................................. 351/160 H

[56] References Cited

PUBLICATIONS

Bard, Allen J., "Photoelectro Chemistry and Heterogeneous Photocatalysis at Semiconductors", Journal of Photochemistry, 10 (1979), pp. 59–75.

Primary Examiner—Conrad J. Clark

[57] ABSTRACT

A contact lens concave-convex in form made of a transparent, optically clear hydrophilic material containing micro-photoelectrolysis elements to produce oxygen by the electrolysis of water.

3 Claims, 3 Drawing Figures

OXYGEN GENERATING CONTACT LENS

THE PRIOR ART

Contact lenses that are being used at this time depend upon the flow of lachrymal fluids around the edge of the lens to supply the cornea with its necessary oxygen. The cornea tissue maintains a temperature much lower than the other body tissues. This is due to evaporation at the corneal surface and the lack of blood supply to the cornea which warms the rest of the body. The temperature of the cornea must be at this lower level or its' metabolic processes will be accelerated. The plastic now being used for fabricating contact lenses is a very poor conductor of heat. This insulating material covering a large percent of the corneal area raises its' temperature which increases the chemical activity of the metabolic processes and the cornea demands more oxygen to maintain normal metabolism. The present lenses prelude the free exchange of atmospheric oxygen dissolved in the precorneal fluid from reaching the corneal tissue. The result is edema and epithelium disorganization.

Lenses have been made with small holes drilled through the lens in an effort to overcome this problem. If the holes are large, they will be seen by the wearer, and if small enough not to be seen, they become clogged with body secretions and are rendered useless.

Silicone and other highly permeable materials are capable of oxygen enrichment if the material has a higher permeability to oxygen than to nitrogen or carbon dioxide.

Present corneal contact lenses must be fitted with the peripheral zone flatter than the cornea in order to provide lachrymal flow and oxygen to the apex of the cornea. This clearance created around the edge allows the lens to move about the cornea and may be forced off center by the action of the upper lid, also lid sensation and discomfort result from edge stand off. With the present corneal contact lenses, no fixed alignment between the optical center of the contact lens and eye is possible.

This new lens design may be employed as a therapeutic device by adding the required medication to the lens material. The medication will be dissolved slowly by the lachrymal fluids and find its' way to the corneal tissue by diffusion to the surface of the lens. Since this lens does not need to be removed, long-lasting and highly effective medications are now possible.

SUMMARY OF THE INVENTION

Natural photosynthesis provides the most obvious example of photochemical solar energy conversion. Field efficiency (yearly average, best crops and so on) is about 1%. These figures are not so high as the efficiency for electricity generation by solid-state photovoltaics. Sunlight-induced photoelectrolysis conversion of water to hydrogen and oxygen approaches the field efficiency of natural photosynthesis. Solid-state photovoltaic devices are the only man-made systems having any wide spread use for solar energy conversion based on electronic excitations. Solid/liquid junction devices represent the best chemical systems for converting light to hydrogen and oxygen from water. The most impressive systems for solar energy conversion to electricity and production of oxygen from water involve the interfacial photoredox events at the junction between semiconductors and liquid electrolyte solutions. Semiconductor/liquid junction cells are different from photogalvanic cells in that light is absorbed by a solid electrode, not by electrolyte species in solution. The most efficient system for the photoelectrolysis of water is the strontium titanium trioxide based cell. The overall efficiency of converting solar energy to hydrogen and oxygen is about 1%. N-type titanium dioxide/p-type gallium phosphorus based cells produce hydrogen and oxygen with no other energy input than the light striking the two electrodes. This type of observation led to the conclusion that "photochemical diodes" consisting of aqueous suspensions of n-type titanium dioxide/p-type gallium phosphorus particles 1-FIG. 3. can yield hydrogen and oxygen from water on optical excitation. Another approach is to sensitize stable semiconductors using visible-light-absorbing dyes attached to the surface. In this approach the aim is to absorb light by a dye layer on the semiconductor surface to produce an excited state; this has been achieved by using zinc oxide sensitized with rose bengal.

The oxygen consumption rate of the human cornea is approximated to be 2.8 ml/cm$^2$-hr. This value has been determined by Jauregui and Fatt, "Estimation of the Vivo Oxygen Consumption of the Human Cornal Epithelium", in the American Journal of Optometry and Archives of American Academy of Optometry, June 1972, page 507.

Figure 3:
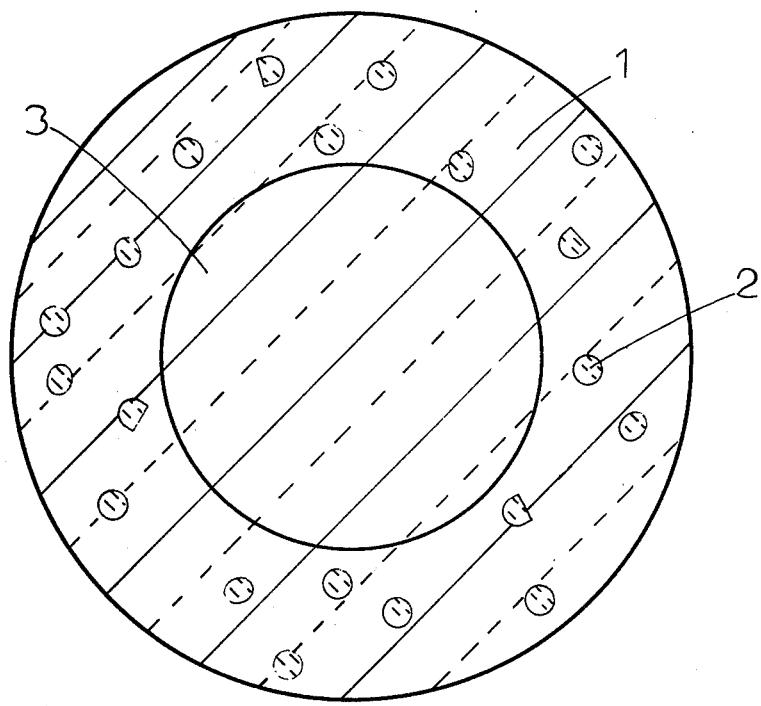
FIG. 3 shows the contact lens from the front.

The carrier of lens material 2-FIG. 3 may be any hydrophilic water containing material. Examples of carrier materials are poly hydroxyethyl methacrylate, poly hydroxypropyl methacrylate, and hydratable polymethylmethacrylate.

Photosensitive particles are suspended in the monomers and a suitable catalyst is added to achieve polymerization. The photosensitive particles are selected from titanium dioxide combined with gallium phosphorus; platinum combined with strontium titanium trioxide, tin oxide combined with a dye; or zinc oxide combined with rose bengal dye. Ferric oxide, titanium dioxide, tin oxide and zinc oxide photoanodes may be used in combination with a nobel metal such as platinum. After polymerization, the lens polymer containing the photosensitive particles imbedded in the periphery are machined into contact lenses having a clear transparent central area 3-FIG. 3 and micro-photosensitive particles surrounding the central optical zone of the lens. After hydration, the liquid semiconductor junction is established at the photosensitive interface and hydrogen and oxygen will be released by the electrolysis of water upon exposure to light.

The rate at which gases are generated must not exceed the solubility limits of the water contained within the lens matrix. Therefore, the efficiency of the photosensitive particals must be kept low to prevent bubbles from forming. The oxygen requirements of the cornea are very low compared to the quanties of oxygen available from the photoelectrochemical decomposition of water. Therefore, a surplus of dissolved oxygen will be available for storage in the lens structure to provide the oxygen requirements of the cornea during sleep.

A sulfonate or a phosphorus group may be incorporated in the polymer matrix to increase the mobility of the water and prevent fouling of the exterior surface. Most debris particles are hydrophobic, or in other words, repel water; most of them also bear a negative electric charge. The most serious debris problems are caused by materials such as oily particles and proteins, which have large surface areas that are hydrophobic, or in other words, repel water. When a hydrophobic substance is in an aqueous environment, it can reduce its' total energy by reducing the area exposed to the water; two hydrophobic particles tend to clump together expelling the water from the space between them and thereby reducing their exposed surface. This phenomena is called hydrophobic bonding. In the same way such a particle can be held to the surface of a contact lens by the elimination of repulsive interactions with the surrounding water. Most of the debris materials also bear a negative electric charge and hydrogen bonding involving these charges also contribute to the buildup of debris. In this kind of bonding the slight positive charge of hydrogen atom at the surface of the lens attracts a negatively charged group in the debris particle.

In liquid water about half the molecules at any moment are in clusters that have the same orderly structure as a crystal of ice. In the clusters, each water molecule is placed so that the oxygen atom occupies the vertex of a tetrahedron and so that a hydrogen bond connects each pair of water molecules. In ice, this stable structure extends over a long distance, but in the liquid state the icelike clusters generally include only a few molecules each, and they are constantly forming and disintegrating. Inside the structure of a negative charged hydrophilic soft lens, the water assumes an icelike state, in which the molecules have an orderly arrangement and are held together by hydrogen bonds. The geometry of the icelike state is tetrahedral, with each oxygen atom surrounded by four others at equal distances. Other molecules and particles are rejected, including not only those that are too large to fit through the lens membrane but also small molecules that cannot conform to the icelike structure. Ions in particular are excluded because they are shielded by a layer of water that would disrupt the icelike lattice. For contact lenses it is desirable to exclude all possible ions and provide only water within the lens structure. Therefore, the materials having the highest contact angle are selected for the lens membrane.

The liquid solid junction is made with the electrolyte contained within the matrix of the polymer material. This provides unique conditions of self regulation and supplying a permanent contamination free liquid to solid interface. These properties separate or together offer many improvements in other applications of solar energy. Self regulation occurs when $O_2$ or $H_2$ are produced at a rate greater than the migration rate into the polymer matrix away from the reaction site where the gases are formed. When undissolved gas accumulates on the surface of the reaction site; the water is displaced and further gas production stops untill the gas dissolves or is free to migrate.

DESCRIPTION OF THE PREFERRED EMBODIMENT

Figure 1:
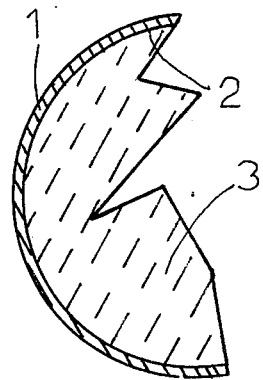
FIG. 1 shows a photosensitive particle in section.
Figure 2:
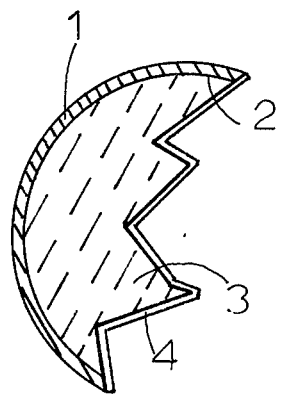
FIG. 2 shows a photosensitive particle in section with a gas layer present.

Photosensitive particles are formed from by coating strontium titanium trioxide pellets, 3 FIGS. 1 and 2, with platinum, 1 FIGS. 1 and 2, and breaking the pellets between metal rollers. The fractured particles are then mixed with the monomer hydroxyethyl methacrylate, 2% of the crosslinkers ethylene dimethacrylate and 0.25% of the catalyst 2, $2^1$ Azobis (2 methylpropionitrite) purged of oxygen, placed under a nitrogen blanket and heated to 55° C. for twelve hours and post cured for 8 hours at 70° C. Contact lenses of concave-convex form having a clear optical zone are fabricated from the material and hydrated. When the lens is exposed to light, an electric potential will be present across the junction, 2 FIGS. 1 and 2, and oxygen, 4 FIG. 2 will be released from the strontium titanium trioxide surface. The water present within the hydrophilic lens material acts as the required electrolyte and as a reservoir for the dissolved oxygen.

Various modifications, of course, can be made without departing from the spirit of this invention or the scope of the appended claims. It is understood that many variations are obtainable which will yield results as disclosed herein. The constants set forth in this disclosure are give as examples and are in no way final or binding.

What is claimed is:

1. A contact lens of concave-convex form in section of a curvature substantially the same as the eye to which it is applied, having a plurality of oxygen emitting light receptors imbedded within the lens structure.

2. A hydrophilic contact lens having a plurality of semiconductor light receptors imbedded within the lens structure, said receptors providing oxygen by the electrolysis of water when activated by light.

3. A contact lens of concave-convex form having a curvature substantially the same as the eye to which it is applied, having a plurality of light absorbing semiconductor receptors imbedded within the peripherial structure of the lens, said light receptors being capable of producing an electrical current when activated by light, and providing oxygen by the decomposition of water by electrolysis.

* * * * *